United States Patent

Andree et al.

[11] Patent Number: 5,847,137
[45] Date of Patent: Dec. 8, 1998

[54] PROCESS FOR PREPARING SUBSTITUTED ARYLURACILS

[75] Inventors: Roland Andree; Mark Wilhelm Drewes, both of Langenfeld; Bernd Gallenkamp, Wuppertal, all of Germany

[73] Assignee: Bayer Aktiengesellschaft, Leverkusen, Germany

[21] Appl. No.: 945,558

[22] PCT Filed: Apr. 22, 1996

[86] PCT No.: PCT/EP96/01669

§ 371 Date: Oct. 27, 1997

§ 102(e) Date: Oct. 27, 1997

[87] PCT Pub. No.: WO96/34859

PCT Pub. Date: Nov. 7, 1996

[30] Foreign Application Priority Data

May 3, 1995 [DE] Germany .......................... 195 16 168.8
Nov. 23, 1995 [DE] Germany .......................... 195 43 676.8

[51] Int. Cl.⁶ .................................................. C07D 239/54
[52] U.S. Cl. .............................................. 544/311; 544/312
[58] Field of Search ...................................... 544/311, 312

[56] References Cited

FOREIGN PATENT DOCUMENTS 562384   10/1995   European Pat. Off. .
4412079   2/1995   Germany .

OTHER PUBLICATIONS

Valkanas et al, J. Amer. Chem. Soc. pp. 1123, 1124, & 1125 (1963).

*Primary Examiner*—John M. Ford
*Attorney, Agent, or Firm*—Sprung Kramer Schaefer & Briscoe

[57] ABSTRACT

The invention relates to a novel process for preparing substituted aryluracils by reacting aminoalkenoic esters with arylurethanes and then with sulfonamides, and additionally to novel 4-(alkoxycarbonylamino)-2,5-difluorobenzonitriles.

7 Claims, No Drawings

PROCESS FOR PREPARING SUBSTITUTED ARYLURACILS

This is a 371 of PCT/EP96/01669, filed Apr. 22, 1996. The invention relates to a novel process for preparing substituted aryluracils known as herbicidally active compounds.

It is known that certain substituted aryluracils such as, for example, 1-(4-cyano-2-fluoro-5-ethylsulfonylaminophenyl)-3,6-dihydro-2,6-dioxo-4-trifluoromethyl-1 (2H)-pyrimidine are obtained when ethyl 3-amino-4,4,4-trifluorocrotonates are reacted with sodium hydride in dimethylformamide/toluene and then with 4-cyano-2,5-difluorophenyl isocyanate and the thus-obtained 1-(4-cyano-2,5-difluoro-phenyl)-3,6-dihydro-2,6-dioxo-4-trifluoromethyl-1(2H)-pyrimidine is reacted with ethanesulfonamide (cf. DE 4412079).

In this preparation, sodium hydride, which is not very suitable for industrial processes, is employed as acid acceptor, and the reaction is carried out as a multi-step reaction.

It has now been found that substituted aryluracils of the general formula (I)

(I)

in which
- $R^1$ represents hydrogen or halogen,
- $R^2$ represents cyano, halogen, thiocarbamoyl or optionally substituted alkyl,
- $R^3$ represents respectively optionally substituted alkyl, alkenyl, alkinyl, cycloalkyl, cycloalkylalkyl, aryl or arylalkyl,
- $R^4$ represents hydrogen, halogen or optionally substituted alkyl and
- $R^5$ represents optionally substituted alkyl, are obtained in good yields and high purity when aminoalkenoic esters of the general formula (II)

(II)

in which
- $R^4$ and $R^5$ are each as defined above and
- R represents alkyl, aryl or arylalkyl, are reacted with arylurethanes (arylcarbamates) of the general formula (III)

(III)

in which
- $R^1$ and $R^2$ are each as defined above,
- R represents alkyl, aryl or arylalkyl and
- X represents halogen, in the presence of a metal alkoxide or a metal carbonate as acid binder and in the presence of an aprotic polar solvent at temperatures between −20° C. and +150° C. ("step one")

and the resulting aryluracil intermediates of the general formula (Ia)

(Ia)

in which
- $R^1$, $R^2$, $R^4$, $R^5$ and X are each as defined above, are then—if appropriate after intermediary isolation— reacted with sulfonamides of the general formula (IV)

$$H_2N—SO_2—R^3,$$ (IV)

in which
- $R^3$ is as defined above,
- in the presence of a metal carbonate as acid binder and in the presence of an aprotic polar solvent at temperatures between 20° C. and 200° C., if appropriate under an atmosphere of inert gas ("step 2").

Surprisingly, the substituted aryluracils of the general formula (I) can be prepared by the process according to the invention in good yields and in high purity in a simpler manner than by the known prior art.

The process according to the invention thus represents a valuable advance on the prior art.

The process according to the invention preferably relates to the preparation of compounds of the formula (I) in which
- $R^1$ represents hydrogen, fluorine, chlorine or bromine,
- $R^2$ represents cyano, fluorine, chlorine, bromine, thiocarbamoyl or optionally fluorine- and/or chlorine-substituted alkyl having 1 to 4 carbon atoms,
- $R^3$ represents respectively optionally cyano-, fluorine-, chlorine-, bromine- or $C_1$–$C_4$-alkoxy-substituted alkyl, alkenyl or alkinyl having in each case up to 6 carbon atoms, represents respectively optionally cyano-, fluorine-, chlorine-, bromine- or $C_1$–$C_4$-alkyl-substituted cycloalkyl or cycloalkylalkyl having 3 to 8 carbon atoms in the cycloalkyl moiety and optionally 1 to 4 carbon atoms in the alkyl moiety, represents aryl or arylalkyl having 6 or 10 carbon atoms in the aryl moiety and optionally 1 to 4 carbon atoms in the alkyl moiety, each of which is optionally substituted by fluorine, chlorine, bromine, cyano, nitro, carboxy, carbamoyl, thiocarbamoyl, by respectively optionally fluorine- and/or chlorine-substituted $C_1$–$C_4$-alkyl, $C_1$–$C_4$-alkoxy, $C_1$–$C_4$-alkylthio, $C_1$–$C_4$-alkylsulfinyl or $C_1$–$C_4$-alkylsulfonyl, by dimethylaminosulfonyl or diethylaminosulfonyl, by optionally fluorine-, chlorine-, bromine-, cyano-, methoxy- or ethoxy-substituted $C_1$–$C_4$-alkoxy-carbonyl, or by respectively optionally fluorine-, chlorine-, bromine-, cyano-, methyl-, methoxy-, trifluoromethyl- and/or trifluoromethoxy-substituted phenyl, phenyloxy or phenylthio, $R^4$ represents hydrogen, fluorine, chlorine, bromine or optionally fluorine- and/or chlorine-substituted alkyl having 1 to 6 carbon atoms and $R^5$ represents optionally fluorine-, chlorine-, bromine-, methoxy- or ethoxy-substituted alkyl having 1 to 6 carbon atoms.

The process according to the invention in particular relates to the preparation of compounds of the formula (I) in which $R^1$ represents hydrogen, fluorine or chlorine, $R^2$ represents cyano, fluorine, chlorine, bromine, thiocarbamoyl, methyl or trifluoromethyl, $R^3$ represents respectively optionally cyano-, fluorine-, chlorine-, methoxy- or ethoxy-substituted methyl, ethyl, n- or i-propyl, n-, i-, s- or t-butyl, ethenyl, propenyl, butenyl, ethinyl, propinyl or butinyl, represents respectively optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, or represents phenyl, naphthyl, benzyl or phenylethyl, each of which is optionally substituted by fluorine, chlorine, bromine, cyano, nitro, carboxy, carbamoyl, thiocarbamoyl, by methyl, ethyl, n- or i-propyl, trifluoromethyl, methoxy, ethoxy, n- or i-propoxy, difluoromethoxy, trifluoromethoxy, methylthio, ethylthio, n- or i-propylthio, methylsulfinyl, ethylsulfinyl, n- or i-propylsulfinyl, methylsulfonyl, ethylsulfonyl, n- or i-propylsulfonyl, by dimethylaminosulfonyl or diethylaminosulfonyl, by methoxycarbonyl, ethoxycarbonyl, n- or i-propoxycarbonyl, $R^4$ represents hydrogen, fluorine, chlorine, bromine, methyl, ethyl or trifluoromethyl and $R^1$ represents methyl, ethyl, trifluoromethyl, chlorodifluoromethyl, fluorodichloromethyl or pentafluoroethyl.

Using, for example, methyl 3-amino-crotonate and N-(4-cyano-2,5-difluoro-phenyl)-O-methyl-urethane and methanesulfonamide as starting materials and potassium carbonate as acid acceptor, the course of the reaction in the process according to the invention can be illustrated by the following scheme:

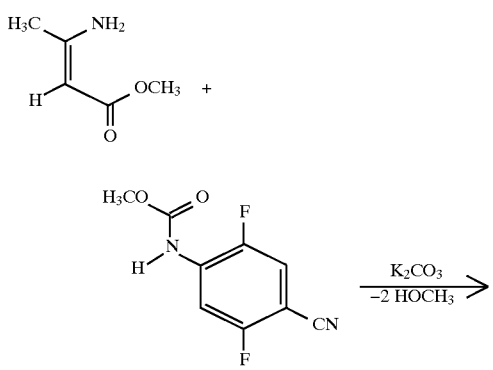

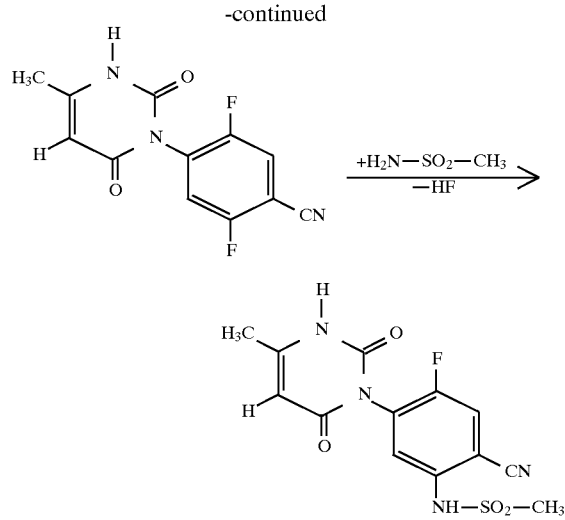

The aminoalkenoic esters to be used as starting materials in the process according to the invention for preparing compounds of the formula (I) are defined in a general way by the formula (II). In the formula (II), $R^4$ and $R^5$ each preferably or in particular have that meaning which has already been indicated above, in the description of the compounds of the formula (I) to be prepared according to the invention, as preferred or as particularly preferred for $R^4$ and $R^5$; R preferably represents $C_1$–$C_4$-alkyl, phenyl or benzyl, in particular methyl, ethyl or phenyl.

The starting materials of the formula (II) are known and/or can be prepared by known processes (cf. J. Hetercycl. Chem. 9 (1972), 513–522).

The arylurethanes further to be used as starting materials in the process according to the invention for preparing compounds of the formula (I) are defined in a general way by the formula (III). In the formula (III), $R^1$ and $R^2$ each preferably or in particular have that meaning which has already been indicated above, in the description of the compounds of the formula (I) to be prepared according to the invention, as preferred or as particularly preferred for $R^1$ and $R^2$; R preferably represents $C_1$–$C_4$-alkyl, phenyl or benzyl, in particular methyl, ethyl or phenyl, X preferably represents fluorine, chlorine or bromine, in particular fluorine or chlorine.

The starting materials of the formula (III) are known and/or can be prepared by known processes (cf. DE 4412079; preparation examples).

The sulfonamides further to be used as starting materials in the process according to the invention for preparing compounds of the formula (I) are defined in a general way by the formula (IV). In the formula (IV), $R^3$ preferably or in particular has that meaning which has already been indicated above, in the description of the compounds of the formula (I) to be prepared according to the invention, as preferred or as particularly preferred for $R^3$.

The starting materials of the formula (IV) are known chemicals for synthesis.

The first step of the process according to the invention is carried out using a metal alkoxide or a metal carbonate as acid binder. Preferred acid binders are alkali metal alkoxides, such as lithium alkoxides, sodium alkoxides and potassium alkoxides having in each case 1 to 5 carbon atoms, in particular sodium methoxide, potassium methoxide, sodium ethoxide, potassium ethoxide, sodium n- or i-propoxide, potassium n- or i-propoxide, sodium n-, i-, s- or t-butoxide, potassium n-, i-, s- or t-butoxide, or alkali metal carbonates or alkaline earth metal carbonates, such as lithium carbonate, sodium carbonate, potassium carbonate, magnesium carbonate and calcium carbonate, in particular potassium carbonate.

The second step of the process according to the invention is carried out using a metal carbonate as acid binder. Preferred acid binders are alkali metal carbonates or alkaline earth metal carbonates, such as lithium carbonate, sodium carbonate, potassium carbonate, magnesium carbonate and calcium carbonate. Potassium carbonate is a very particularly preferred acid binder.

Both steps of the process according to the invention are carried out in the presence of an aprotic polar solvent. Specific examples of these solvents are: ketones such as methyl ethyl ketone, methyl i-propyl ketone and methyl i-butyl ketone, esters such as ethyl acetate, n- or i-propyl acetate and n-, i- or s-butyl acetate, nitriles such as acetonitrile, propionitrile and butyronitrile, amides such as dimethylformamide and dimethylacetamide, furthermore dimethyl sulfoxide, tetramethylene sulfone (sulfolane), N-methyl-pyrrolidone and hexamethylphosphoric triamide. N-methyl-pyrrolidone is a very particularly preferred solvent for the process according to the invention.

The reaction temperatures in the practice of step 1 of the process according to the invention can be varied within a relatively wide range. Generally, the reaction is carried out at temperatures between −20° C. and 100° C., preferably between 0° C. and 80° C., in particular between 0° C. and 60° C.

The reaction temperatures in the practice of step 2 of the process according to the invention can also be varied within a relatively wide range. Generally, the reaction is carried out at temperatures between 20° C. and 200° C., preferably between 50° C. and 180° C., in particular between 80° C. and 160° C.

Both steps of the process according to the invention are generally carried out at atmospheric pressure. However, it is also possible to carry out the process according to the invention at elevated or reduced pressure—generally between 0.1 bar and 10 bar.

In the practice of the process according to the invention for preparing the substituted aryluracils of the formula (I), generally between 0.5 and 1.5 mol, preferably between 0.7 and 1.3 mol, of the arylurethane of the formula (III) and between 0.5 and 2.0 mol, preferably between 0.8 and 1.5 mol, of the sulfonamide of the formula (IV) are employed per mole of aminoalkenoic ester of the formula (II).

In a preferred embodiment of the process according to the invention, the aminoalkenoic ester of the formula (II) is heated with stirring to about 100° C. with an alkali metal carbonate or alkaline earth metal carbonate in an aprotic polar solvent. An arylurethane of the formula (III) is then added and the mixture is heated for some time to a slightly higher temperature—about 120° C. to 150° C.—, the alcohol liberated during the reaction being removed by distillation. Subsequently, a sulfonamide of the formula (IV) and optionally an alkali metal carbonate or alkaline earth metal carbonate are added and the mixture is stirred further at the abovementioned elevated temperature until the reaction has ended.

The mixture is then diluted with water and washed with a virtually water-immiscible organic solvent such as, for example, methylene chloride, the aqueous phase is acidified with a strong acid such as, for example, hydrochloric acid and extracted with a virtually water-immiscible organic solvent such as, for example, methylene chloride, and the extract is washed with water and concentrated using water pump vacuum. The residue is digested with water and the crystalline product is isolated by filtration with suction.

The substituted aryluracils to be prepared by the process according to the invention are already known as herbicidally active compounds (cf. DE 4412079).

PREPARATION EXAMPLES

Example 1

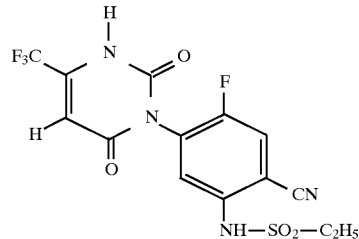

Under a nitrogen atmosphere, a mixture of 27.6 g (0.15 mol) of ethyl 3-amino-4,4,4-trifluoro-crotonate, 27.6 g (0.20 mol) of potassium carbonate (powder) and 100 ml of N-methyl-pyrrolidone is stirred at 100° C. for one hour. 22.8 g (0.10 mol) of N-(4-cyano-2,5-difluoro-phenyl)-O-ethyl-urethane are then added and the mixture is stirred at 130° C. for about 4 hours using a water separator to distill off ethanol. Subsequently, 16.4 g (0.12 mol) of ethanesulfonamide (80% pure) and 13.8 g (0.10 mol) of potassium carbonate (powder) are added at 130° C., and the mixture is stirred for 2 hours at 130° C. and for a further 16 hours at 140° C. After the reaction has ended, the mixture is poured into 750 ml of water and washed three times with 250 ml of methylene chloride each time. The aqueous phase is acidified with about 10% strength hydrochloric acid and extracted three times with 300 ml of methylene chloride each time. The combined organic phases are washed two times with 250 ml of water each time and concentrated using water pump vacuum. The residue is stirred with 250 ml of water and the crystalline product is isolated by filtration with suction.

28.3 g (70% of theory) of 1-(4-cyano-5-ethylsulfonylamino-2-fluorophenyl)-3,6-dihydro-2,6-dioxo-4-trifluoromethyl-1(2H)-pyrimidine of melting point 228° C. are obtained.

Example 2

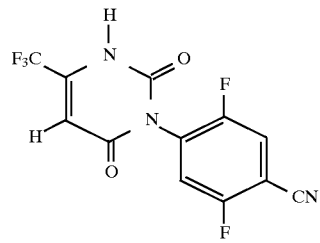

184 g of sodium methoxide (97% pure, 3.3 mol) are suspended in 2000 ml of N-methyl-pyrrolidone (NMP) and, at 0° C. to 5° C., admixed with a solution of 617 g of ethyl 3-amino-4,4,4-trifluoro-crotonate (98% pure, 3.3 mol) in 100 ml of NMP over a period of about 90 minutes. The mixture is stirred at room temperature (about 20° C.) for about 60 minutes and then heated to about 125° C. to distill off methanol, the internal temperature slowly increasing to about 120° C. After about 90 minutes, 632 g of N-(4-cyano-2,5-difluoro-phenyl)-O-ethyl-urethane (98% pure, 2.75 mol) are added to the mixture and the reaction mixture is then stirred at 135° C. to 140° C. for about five hours to remove most of the liberated alcohol by distillation. Most of the NMP is then distilled off, the residue is taken up in 14 liters of water and, after the addition of 1 liter of i-propanol, slowly acidified with 10% strength hydrochloric acid (about 750 ml). The mixture is stirred at 20° C. for two hours, left to stand for about 15 hours and then filtered with suction. The crude solid product is suspended in 2750 ml of i-propanol and the mixture is stirred for two hours at reflux and for a further about 15 hours at about 20° C. The purified product is then isolated by filtration with suction.

549 g (63% of theory) of 1-(4-cyano-2,5-difluoro-phenyl)-3,6-dihydro-2,6-dioxo-4-trifluoromethyl-1(2H)-pyrimidine of melting point 194° C. are obtained.

Example 3

(step two)

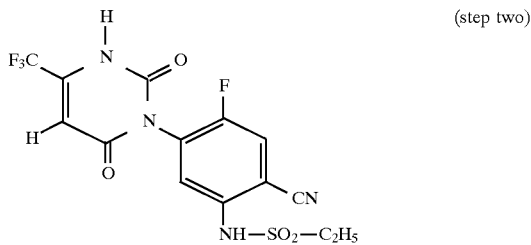

333 g of 1-(4-cyano-2,5-difluoro-phenyl)-3,6-dihydro-2,6-dioxo-4-trifluoromethyl-1(2H)-pyrimidine (1.05 mol) and 201 g of ethanesulfonamide (1.47 mol) are dissolved in 1050 ml of N-methyl-pyrrolidone (NMP) and admixed with 435 g of potassium carbonate (3.15 mol). The mixture is then stirred at 135° C. for 16 hours. Most of the NMP is then distilled off and the residue is taken up in 7.5 liters of water, admixed with 250 ml of methylene chloride, acidified with 10% strength hydrochloric acid and stirred at about 20° C. for 2 hours. The crystalline product is then isolated by filtration with suction.

355 g (96.7% pure, 80.5% of theory) of 1-(4-cyano-5-ethylsulfonylamino-2-fluoro-phenyl)-3,6-dihydro-2,6-dioxo-4-trifluoromethyl-1(2H)-pyrimidine of melting point 228° C. are obtained.

Example 4

(step two)

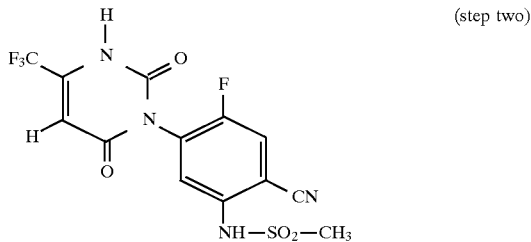

190 g of 1-(4-cyano-2,5-difluoro-phenyl)-3,6-dihydro-2,6-dioxo-4-trifluoromethyl-1(2H)-pyrimidine (97.2% pure, 0.58 mol) and 68.5 g of methanesulfonamide (96.4% pure, 0.70 mol) are dissolved in 800 ml of N-methyl-pyrrolidone (NMP) and admixed with 328 g of potassium carbonate (2.37 mol). The mixture is then stirred at 135° C. for 17 hours. Most of the NMP is then distilled off and the residue is taken up in 2.75 liters of water, admixed with 1500 ml of methylene chloride, acidified with 10% strength hydrochloric acid and stirred at about 20° C. for two hours. The crystalline product is then isolated by filtration with suction (1st product fraction).

84.5 g (98.9% pure) of 1-(4-cyano-5-methylsulfonylamino-2-fluoro-phenyl)-3,6-dihydro-2,6-dioxo-4-trifluoromethyl-1(2H)-pyrimidine of melting point 248° C. are obtained.

The filtrate is shaken, the organic phase is separated off, the aqueous phase is shaken with methylene chloride and the combined organic phases are washed with water and then concentrated. The residue is stirred with 1.5 liters of water and 150 ml of i-propanol for three hours; the crystalline product is then isolated by filtration with suction (2nd product fraction).

178 g (92.1% pure) of 1-(4-cyano-5-methylsulfonylamino-2-fluoro-phenyl)-3,6-dihydro-2,6-dioxo-4-trifluoromethyl-1(2H)-pyrimidine of melting point 248° C. are obtained.

Total yield: (80% of theory).

Starting materials of formula (III)

Example (III-1)

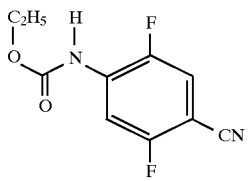

630 g of 4-amino-2,5-difluoro-benzonitrile (97.8% pure, 4.0 mol) and 475 g of pyridine (6.0 mol) are dissolved in 4000 ml of methylene chloride and, at 0° C. to 10° C., admixed with 488 g of ethyl chloroformate (98% pure, 4.4 mol) over a period of about two hours. The reaction mixture is then stirred at about 20° C. for about 15 hours. After the addition of a further 11 g of ethyl chloroformate, the mixture is stirred at 20° C. for a further two hours, diluted with 5 liters of methylene chloride, washed two times with 1250 ml of 3% strength hydrochloric acid each time and once with 1250 ml of water, and the organic phase is concentrated. The residue is stirred with 600 ml of methyl t-butyl ether (MTBE) for one hour and the crystalline product is then isolated by filtration with suction.

793 g of 4-(ethoxycarbonylamino)-2,5-difluoro-benzonitrile (98.5% pure, 86% of theory) of melting point 107° C. are obtained.

4-(Methoxycarbonylamino)-2,5-difluoro-benzonitrile of melting point 129° C. is obtained in a similar manner.

The compounds that can be prepared by the method of Example (III-1)—4-(methoxycarbonylamino)-2,5-difluoro-benzonitrile and 4-(ethoxycarbonylamino)-2,5-difluoro-benzonitrile— have not been disclosed in the literature; as novel compounds they also form part of the subject matter of the present application.

We claim:

1. Process for preparing substituted aryluracils of the general formula (I)

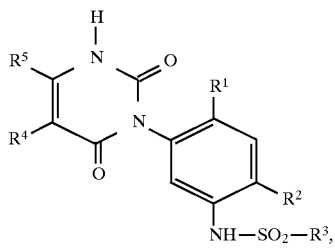

in which $R^1$ represents hydrogen or halogen, $R^2$ represents cyano, halogen, thiocarbamoyl or optionally substituted alkyl, $R^3$ represents respectively optionally substituted alkyl, alkenyl, alkinyl, cycloalkyl, cycloalkylalkyl, aryl or arylalkyl, $R^4$ represents hydrogen, halogen or optionally substituted alkyl and $R^5$ represents optionally substituted alkyl, characterized in that aminoalkenoic esters of the general formula (II)

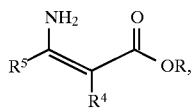

in which $R^4$ and $R^5$ are each as defined above and

R represents alkyl, aryl or arylalkyl, are reacted with arylurethanes (arylcarbamates) of the general formula (III)

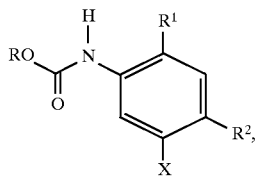

in which $R^1$ and $R^2$ are each as defined above,

R represents alkyl, aryl or arylalkyl and

X represents halogen, in the presence of a metal alkoxide or a metal carbonate as acid binder and in the presence of an aprotic polar solvent at temperatures between −20° C. and +150° C. ("step one")

and the resulting aryluracil intermediates of the general formula (Ia)

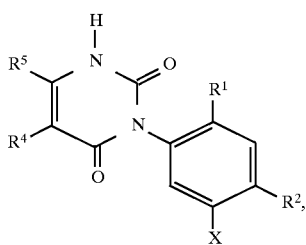

in which $R^1$, $R^2$, $R^4$, $R^5$ and X are each as defined above, are then—if appropriate after intermediary isolation—reacted with sulfonamides of the general formula (IV)

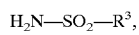

in which $R^3$ is as defined above, in the presence of a metal carbonate as acid binder and in the presence of an aprotic polar solvent at temperatures between 20° C. and 200° C., if appropriate under an atmosphere of inert gas ("step 2").

2. Process for preparing substituted aryluracils of the general formula (I) according to claim 1, characterized in that $R^1$ represents hydrogen, fluorine, chlorine or bromine, $R^2$ represents cyano, fluorine, chlorine, bromine, thiocarbamoyl or optionally fluorine- and/or chlorine-substituted alkyl having 1 to 4 carbon atoms, $R^3$ represents respectively optionally cyano-, fluorine-, chlorine-, bromine- or $C_1$–$C_4$-alkoxy-substituted alkyl, alkenyl or alkinyl having in each case up to 6 carbon atoms, or represents respectively optionally cyano-, fluorine-, chlorine-, bromine- or $C_1$–$C_4$-alkyl-substituted cycloalkyl or cycloalkylalkyl having 3 to 8 carbon atoms in the cycloalkyl moiety and optionally 1 to 4 carbon atoms in the alkyl moiety, represents aryl or arylalkyl having 6 or 10 carbon atoms in the aryl moiety and optionally 1 to 4 carbon atoms in the alkyl moiety, each of which is optionally substituted by fluorine, chlorine, bromine, cyano, nitro, carboxy, carbamoyl, thiocarbamoyl, by respectively optionally fluorine- and/or chlorine-substituted $C_1$–$C_4$-alkyl, $C_1$–$C_4$-alkoxy, $C_1$–$C_4$-alkylthio, $C_1$–$C_4$-alkylsulfinyl or $C_1$–$C_4$-alkylsulfonyl, by dimethylaminosulfonyl or diethylaminosulfonyl, by optionally fluorine-, chlorine-, bromine-, cyano-, methoxy- or ethoxy-substituted $C_1$–$C_4$-alkoxy-carbonyl, or by respectively optionally fluorine-, chlorine-, bromine-, cyano-, methyl-, methoxy-, trifluoromethyl- and/or trifluoromethoxy-substituted phenyl, phenyloxy or phenylthio, $R^4$ represents hydrogen, fluorine, chlorine, bromine or optionally fluorine- and/or chlorine-substituted alkyl having 1 to 6 carbon atoms and $R^5$ represents optionally fluorine-, chlorine-, bromine-, methoxy- or ethoxy-substituted alkyl having 1 to 6 carbon atoms.

3. Process for preparing substituted aryluracils of the general formula (I) according to claim 1, characterized in that $R^1$ represents hydrogen, fluorine or chlorine, $R^2$ represents cyano, fluorine, chlorine, bromine, thiocarbamoyl, methyl or trifluoromethyl, $R^3$ represents respectively optionally cyano-, fluorine-, chlorine-, methoxy- or ethoxy-substituted methyl, ethyl, n- or i-propyl, n-, i-, s- or t-butyl, ethenyl, propenyl, butenyl, ethinyl, propinyl or butinyl, or represents respectively optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, or represents phenyl, naphthyl, benzyl or phenylethyl, each of which is optionally substituted by fluorine, chlorine, bromine, cyano, nitro, carboxy, carbamoyl, thiocarbamoyl, by methyl, ethyl, n- or i-propyl, trifluoromethyl, methoxy, ethoxy, n- or i-propoxy, difluoromethoxy, trifluoromethoxy, methylthio, ethylthio, n- or i-propylthio, methylsulfinyl, ethylsulfinyl, n- or i-propylsulfinyl, methylsulfonyl, ethylsulfonyl, n- or i-propylsulfonyl, by dimethylaminosulfonyl or diethylaminosulfonyl, by methoxycarbonyl, ethoxycarbonyl, n- or i-propoxycarbonyl, $R^4$ represents hydrogen, fluorine, chlorine, bromine, methyl, ethyl or trifluoromethyl and $R^5$ represents methyl, ethyl, trifluoromethyl, chlorodifluoromethyl, fluorodichloromethyl or pentafluoroethyl.

4. Process for preparing 1-(4-cyano-5-ethylsulfonylamino-2-fluorophenyl)-3,6-dihydro-2,6-dioxo-4-methyl-1(2H)-pyrimidine according to claim 1, characterized in that methyl 3-amino-crotonate and N-(4-cyano-2,5-difluorophenyl)-O-methyl-urethane and methanesulfonamide as starting materials and potassium carbonate as acid acceptor are reacted according to the following scheme:

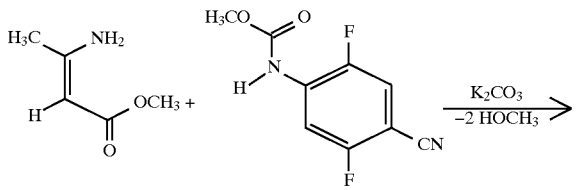

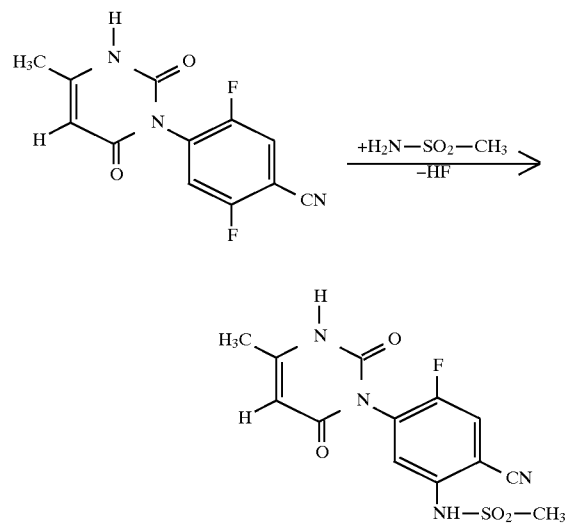

5. Process for preparing substituted aryluracils according to claim 1, characterized in that the reaction temperature of step 1 of the reaction varies in the range between 0° C. and 80° C. and the reaction temperature of step 2 of the reaction varies in the range between 50° C. and 180° C.

6. Process for preparing substituted aryluracils according to claim 1, characterized in that the process is carried out at atmospheric pressure.

7. Process for preparing substituted aryluracils according to claim 1, characterized in that between 0.5 and 1.5 mol of arylmethane of the formula (III) and between 0.5 and 2.0 mol of sulfonamide of the formula (IV) are employed per mole of aminoalkenoic ester of the formula (II).

* * * * *